(12) United States Patent
Hajianpour

(10) Patent No.: US 7,001,395 B2
(45) Date of Patent: Feb. 21, 2006

(54) MEDULLARY PLUG INCLUDING AN EXTERNAL SHIELD AND AN INTERNAL VALVE

(76) Inventor: Mohammed A. Hajianpour, 1706 Vestal Dr., Coral Springs, FL (US) 33071

( * ) Notice: Subject to any disclaimer, the term of this patent is extended or adjusted under 35 U.S.C. 154(b) by 345 days.

(21) Appl. No.: 10/300,260

(22) Filed: Nov. 20, 2002

(65) Prior Publication Data
US 2003/0097136 A1    May 22, 2003

Related U.S. Application Data

(63) Continuation-in-part of application No. 09/590,039, filed on Jun. 8, 2000, now Pat. No. 6,506,194.

(51) Int. Cl.
*A61B 17/56* (2006.01)
(52) U.S. Cl. ..................................... 606/95
(58) Field of Classification Search ............ 606/92, 606/94, 95, 195; 604/103.05, 104
See application file for complete search history.

(56) References Cited

U.S. PATENT DOCUMENTS

| | | |
|---|---|---|
| 4,276,659 A | 7/1981 | Hardinge |
| 4,447,915 A | 5/1984 | Weber |
| 4,627,434 A | 12/1986 | Murray |
| 4,697,584 A | 10/1987 | Haynes |
| 5,059,193 A | 10/1991 | Kuslich |
| 5,383,932 A | 1/1995 | Wilson et al. |
| 5,662,657 A | 9/1997 | Carn |
| 5,766,178 A | 6/1998 | Michielli et al. |
| 5,782,917 A | 7/1998 | Carn |
| 5,849,014 A | 12/1998 | Mastrorio et al. |
| 5,861,043 A | 1/1999 | Carn |
| 5,879,403 A | 3/1999 | Ostiguy et al. |
| 5,935,169 A | 8/1999 | Chan |
| 5,980,530 A * | 11/1999 | Willard et al. .............. 623/1.11 |
| 5,997,580 A | 12/1999 | Mastrorio et al. |
| 6,227,860 B1 | 5/2001 | Hobo |
| 6,251,141 B1 | 6/2001 | Pierson, III et al. |

* cited by examiner

*Primary Examiner*—Glenn K. Dawson
*Assistant Examiner*—D. Jacob Davis
(74) *Attorney, Agent, or Firm*—Ronald V. Davidge

(57) ABSTRACT

A plug for stopping the flow of bone cement in a channel within bone includes an elastomeric inflatable structure protected from bone fragments and sharp edges by a shield extending around the inflatable structure. The shield may be formed as two or more coaxial structures having flexible members extending between opposite ends, with flexible members from an inner such structure curving outward to lie between adjacent flexible members from an outer such structure as the inflatable structure is inflated. The core is also removably connected to an insertion tool, with passageways in the insertion tool and in the core being used to insert a fluid into the inflatable structure. A valve extends as a sleeve around the core, and over the passageway, allowing fluid to flow into the inflatable structure, but preventing it from flowing out of the inflatable structure.

20 Claims, 7 Drawing Sheets

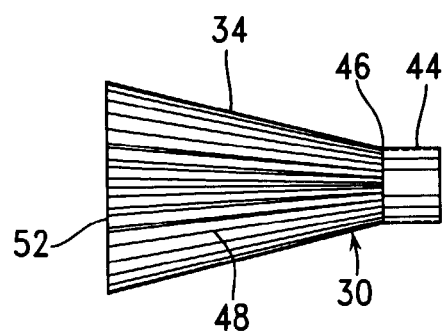
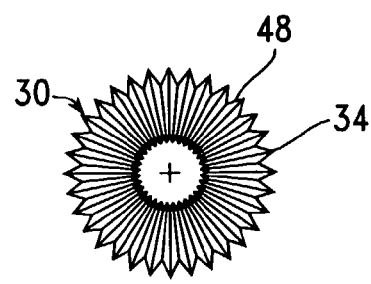
FIG. 3  FIG. 4
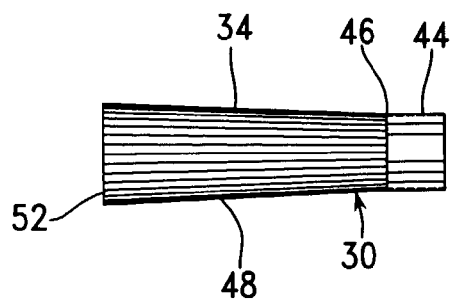
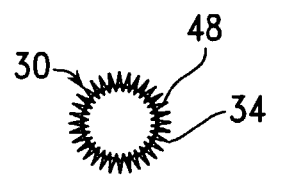
FIG. 5  FIG. 6
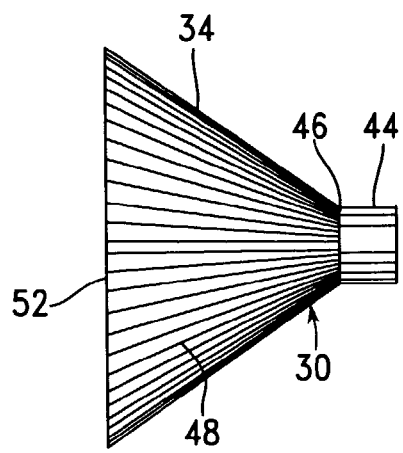
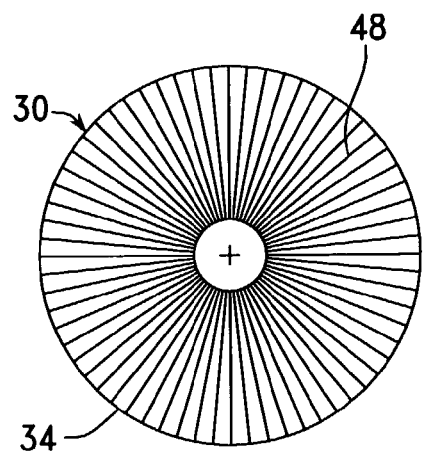
FIG. 7  FIG. 8

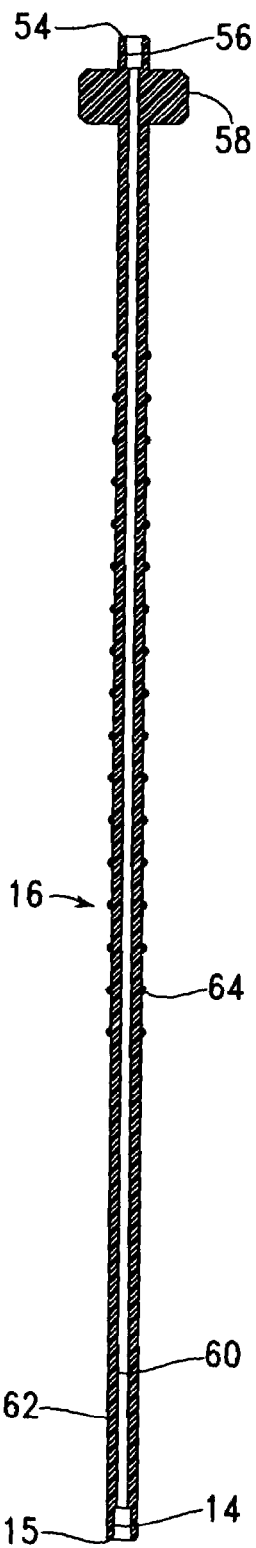
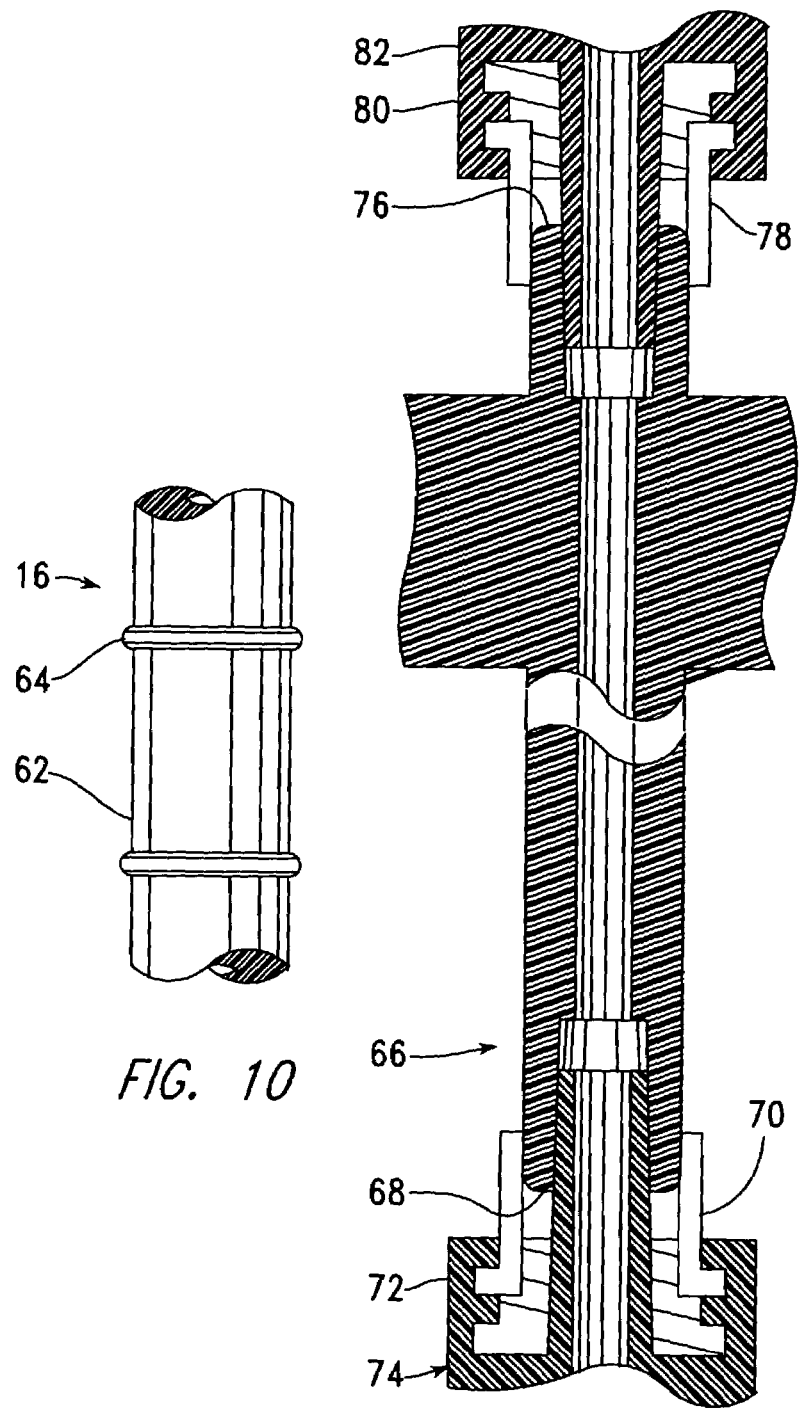
FIG. 9   FIG. 10   FIG. 11

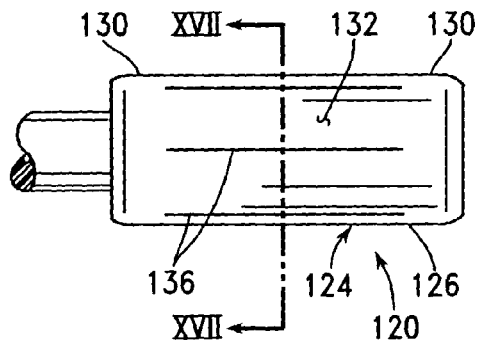
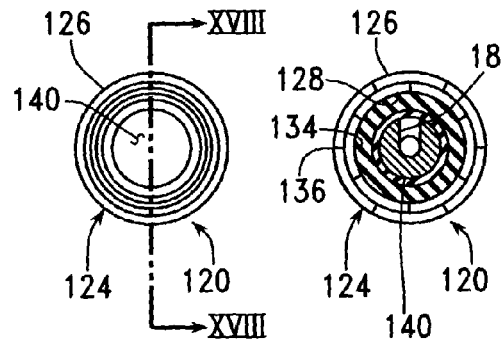
FIG. 15    FIG. 16    FIG. 17
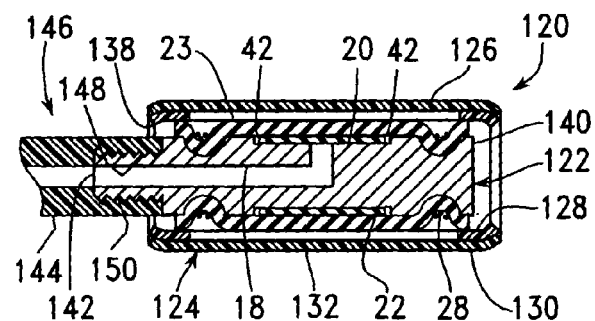
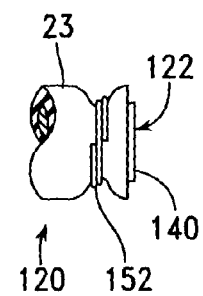
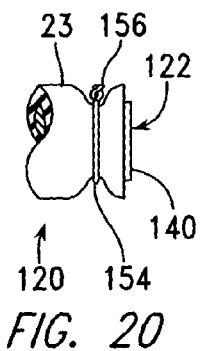
FIG. 18    FIG. 19    FIG. 20
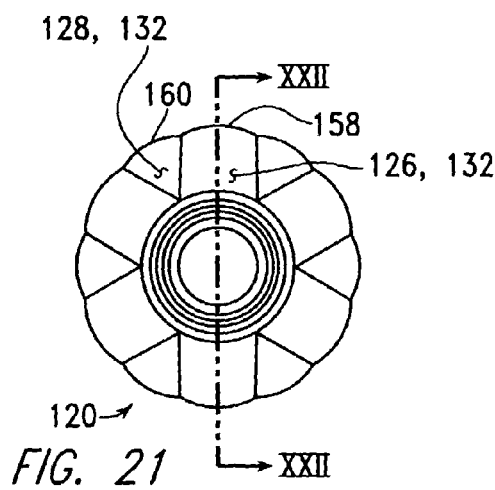
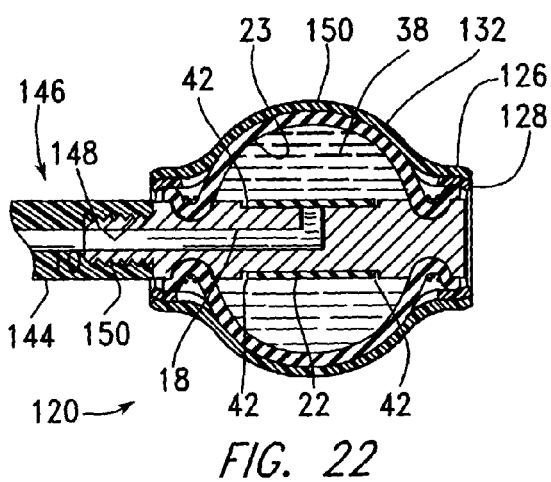
FIG. 21    FIG. 22

MEDULLARY PLUG INCLUDING AN EXTERNAL SHIELD AND AN INTERNAL VALVE

CROSS-REFERENCE TO RELATED APPLICATIONS

This is a continuation-in-part of application Ser. No. 09/590,039, filed Jun. 8, 2000 now U.S. Pat. No. 6,506,194, for which a Notice of Allowance has been received.

This is also related to application Ser. No. 09/730,972, filed Dec. 6, 2000, which is incorporated herein by reference.

BACKGROUND INFORMATION

1. Field of Invention

This invention relates to medical apparatus for use in the implantation of a joint prosthesis to the end of a bone and, more particularly, to a plug for stopping the flow of bone cement, used in the attachment of a prosthesis, at a predetermined point within the intramedullary bone channel.

2. Description of the Related Art

A number of U.S. Patents describe apparatus for plugging the open end of an intramedullary bone canal to restrict the flow of bone cement during the insertion of bone cement, particularly during the pressurized injection of such a cement during an operative procedure involving the fixation of the stem of an artificial joint prosthesis to the end of a bone such as in the fixation of a hip joint prosthesis to the proximal femur.

For example, U.S. Pat. No. 4,697,584 describes an inflatable bone plug which is inflated with a fluid capable of escaping from the plug within a relatively short period of time after the bone cement holding the prosthesis in place has hardened to avoid possible weakening of the cortical bone surrounding the inflated plug. This invention also relates to an inflatable bone plug of the above type which is preferably constructed from a silicone elastomer and is pressurized with carbon dioxide gas. However, for substantial inflation to occur in the desired manner, the bone plug is made of an elastomeric material. Such materials, which have elastic properties allowing substantial elongation, are subject to cutting and puncturing due to bone splinters and sharp edges in a channel cut into bone, as the plug is moved into position within the channel. Furthermore, the use of an internal valve associated with a needle for injecting a fluid complicates the manufacture of the inflatable bone plug.

U.S. Pat. No. 5,849,014 describes a cement restrictor system including an inflatable body, a conduit having first and second ends that defines a fluid passage to and from the inflatable body, and a shield releasably securable to the conduit. In an exemplary method of making a cement plug with the system an obstruction, such as the shield, is placed in a medullary canal of a long bone beyond the isthmus of the long bone. The obstruction is held in place with the inflatable body. A predetermined quantity of bone cement is poured into the medullary canal and localized by the obstruction. The bone cement is allowed to harden; and the conduit and inflatable body are removed from the bone. Again, the inflatable body is elastomeric and is not protected from cutting or puncturing by bone splinters and sharp edges as the restrictor system is moved into place within a bone channel, with the inflatable body preceding the shield. Also, the separate formation of a bone plug from cement and subsequent removal of the conduit and inflatable body to allow insertion of the prosthesis may lengthen the time required for a hip replacement procedure.

U.S. Pat. No. 5,935,169 describes a bone cement plug including a core having a substantially cylindrically-shaped base portion defining a threaded bore therein extending axially and distally from a proximal end of the base portion; a first leg portion depending from and extending distally from the base portion; and a second leg portion depending from and extending distally from the base portion and opposed to the first leg portion; the base portion threaded bore being adapted to receive an expander screw to wedge apart the first and second leg portions, whereby to expand the core widthwise to secure the plug in the bone canal; and the expander screw, the screw comprising a generally cylindrically-shaped body having a tapered distal end, and a proximal end in which is disposed a threaded bore, external threads disposed on the body, and an annular flange extending outwardly from the proximal end of the body, the screw being threadedly engageable with the core threaded bore for advancement of the screw into the plug for the wedging apart of the first and second legs. A method is also disclosed for using the bone cement plug to compact bone cement into a bone canal during total joint replacement surgeries. However, this type of bone cement plug, having a finite number, such as two, mechanically coupled legs to expand, cannot have the flexibility of a system using an inflatable plug in terms of forming a proper seal within a bone channel which may not be round and smooth, and which varies locally in radius.

U.S. Pat. No. 5,997,580 describes a cement restrictor including a member or body that is expandable or transitionable from a first diameter to a second diameter. The cement restrictor includes a single or multiple finned body having a first stable state and a second stable state. In the first stable state, the cement restrictor is narrower than in the second stable state. While the cement restrictor is readily transitionable from the first stable state to the second stable state, the transition can be irreversible. An illustrative embodiment of the cement restrictor includes a body having a first end and a second end. Bistable fins extend radially from the body and are irreversibly movable from a first stable state to a second stable state. The fins are concave with respect to the first end of the body in the first stable state and convex with respect to the first end of the body in the second stable state. The diameter of each fin is larger in the second stable state than in the first stable state. Other embodiments of inventive cement restrictors are shown that include shape memory material that changes shape or dimension(s) in response to temperature and/or stress. However, the expansion of the cement restrictor is limited to the transition between the first stable state and the second stable state, together with elastic and plastic deformation of the material. This method thus does not offer the kind of flexibility of a system with an inflatable body in expansion to meet varying conditions within the bone channel. Furthermore, the time required to apply liquids at different temperatures to make the transitionable body perform as desired may increase the time required for hip replacement surgery.

A number of patents describe bone plugs including a central core from which a number of disks extend as fins at spaced locations. Examples of such devices are found in U.S. Pat. Nos. 5,383,932, 5,662,657, 5,766,178, 5,782,917, 5,861,043, 5,879,403. Such systems allow only deformation of the individual disks to compensate for changes in the shape of the bone channel, such as out-of-round conditions and changes in hole diameter. Therefore, such systems cannot compensate for such conditions to the extent possible with systems including inflatable bodies.

SUMMARY OF THE INVENTION

It is therefore a first objective of the present invention to provide a bone plug having an elastomeric inflatable structure which is protected from puncture by bone splinters and sharp bone edges by a flexible but tough shield extending around the inflatable structure as it is inserted within a bone channel.

It is a second objective of the present invention to provide a bone plug having a shield structure which can expand greatly without significantly stretching the material from which it is made.

It is a third objective of the present invention to provide a bone plug having an elastomeric inflatable structure which is easily manufactured.

It is a fourth objective of the present invention to provide a bone plug and an associated insertion tool which are easily disconnected when the bone plug has been inserted into a proper position.

According to a first aspect of the present invention, there is provided apparatus for plugging a channel within a bone to stop the flow of bone cement through the channel. The apparatus includes a bone plug and an elongated insertion tool. The bone plug, which is insertable within the channel, includes an inflatable structure, a core attached to the inflatable structure, having a distal portion extending beyond a distal end of the inflatable structure, a shield extending from the distal portion of the core outwardly around and along the inflatable structure, and a valve admitting a fluid into the inflatable structure and preventing a flow of the fluid from the inflatable structure. The core includes a core passageway for the fluid injected into the inflatable. The shield, which is substantially more resistant to damage from sharp objects than the inflatable structure, includes a number of coaxial shield structures, each of which includes a distal end portion, a proximal end portion, and a number of flexible beam portions extending longitudinally along the inflatable structure between the distal end portion and the proximal end portion. The flexible beam portions of the coaxial shield structures curve outwardly with inflation of the inflatable structure, with central portions of the flexible beam portions within each of the coaxial shield structures separating from one another, and with the central portions of the flexible beam portions of one of the coaxial shield structures extending outward between adjacent central portions of another of the coaxial shield structures. The elongated insertion tool, which is removably connected to the core, includes a tool passageway for the fluid injected into the core passageway.

BRIEF DESCRIPTION OF THE DRAWINGS

FIG. 3 is a side elevation of a shield of the bone plug of FIG. 1 in an undeflected condition;

FIG. 4 is a proximal end elevation of the shield of FIG. 3 in an undeflected condition;

FIG. 5 is a side elevation of the shield of FIG. 3 in a fully compressed condition;

FIG. 6 is a proximal end elevation of the shield of FIG. 3 in a fully compressed condition;

FIG. 7 is a side elevation of the shield of FIG. 3 in a fully extended condition;

FIG. 8 is a proximal end elevation of the shield of FIG. 3 in a fully extended condition;

FIG. 9 is a longitudinal cross-sectional elevation of an insertion device used to insert the bone plug of FIG. 1 into a previously-prepared channel within a bone;

FIG. 10 is a fragmentary side elevation of the insertion device of FIG. 9;

FIG. 11 is a fragmentary longitudinal cross-sectional elevation of an alternative insertion device used to insert the bone plug of FIG. 1 into a previously-prepared channel within a bone;

FIG. 15 is a side elevation of a bone plug made in accordance with a third embodiment of the present invention in a fully deflated condition;

FIG. 16 is a distal end elevation of the bone plug of FIG. 15 in a fully deflated condition;

FIG. 17 is a transverse cross-sectional view of the bone plug of FIG. 15 in a fully deflated condition, taken as indicated by section lines XVII—XVII therein;

FIG. 18 is a longitudinal cross-sectional view of the bone plug of FIG. 15 in a fully deflated condition, taken as indicated by section lines XVIII—XVIII in FIG. 16;

FIG. 19 is a fragmentary longitudinal elevation of a central portion of the bone plug of FIG. 15, showing a first version of a retaining band to hole an inflatable structure in place on a core therein;

FIG. 20 is a fragmentary longitudinal elevation of a central portion of the bone plug of FIG. 15, showing a second version of a retaining band to hole an inflatable structure in place on a core therein;

FIG. 21 is a distal end elevation of the bone plug in FIG. 15 in a fully inflated condition;

FIG. 22 is a longitudinal cross-sectional view of the bone plug of FIG. 15, in a fully inflated condition, taken as indicated by section lines XXII—XXII in FIG. 21;

DESCRIPTION OF THE INVENTION

Figure 1:
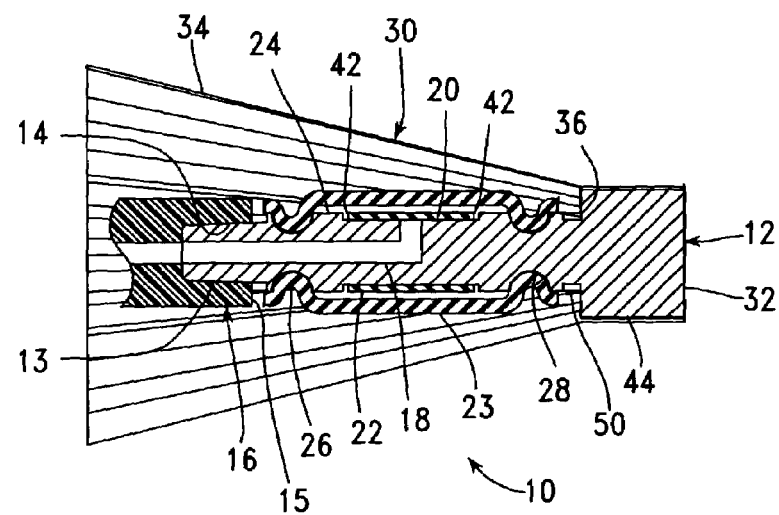
FIG. 1 is a longitudinal cross-sectional view of a bone plug made in accordance with a first embodiment of the present invention with an inflatable sleeve of the bone plug in a fully deflated condition.

FIG. 1 is a longitudinal cross-sectional view of a bone plug, generally indicated as 10, made in accordance with a first embodiment of the present invention. The bone plug 10 includes a generally cylindrical core 12 having a tapered proximal end 13 which is removably attached to a mating tapered hole 14 at a distal end 15 of an insertion device, generally indicated as 16. The core 12 includes an "L"-shaped internal passage 18, extending between the tapered proximal end 13 and a cylindrical surface 20 extending under an elastomeric valve sleeve 22. The core 12 is preferably composed of a molded thermoplastic material such as acetal or high-density polyethylene. A generally cylindrical inflatable elastomeric sleeve 23 extends along a central portion 24 of the core 12, being held in place by internal ridges 26, which extend within grooves 28 in the core 12. The grooves 28 extend around the circumference of the core 12. The internal ridges 26 may also be attached by means of an adhesive within the grooves 28. The bone plug 10 also includes a shield 30 fastened, preferably by ultrasonic welding or by means of an adhesive, to a cylindrical distal end 32 of the core 12. A conical portion 34 of the shield 30 is expandable and compressible from the undeflected condition in which it is shown in FIG. 1.

Preferably, a specific provision is made to make the bone plug 10 visible during X-ray examination. For example, a stainless-steel ring 36 is included as an insert in the mold making the core 12. Alternately, a radiopaque coating may be applied to a portion of the core 12, or radiopaque fillers may be molded into the core 12. During installation of the bone plug 10 into a cannel within bone, X-ray examination may be used to determine if the correct placement of the plug 10 has been achieved.

Figure 2:
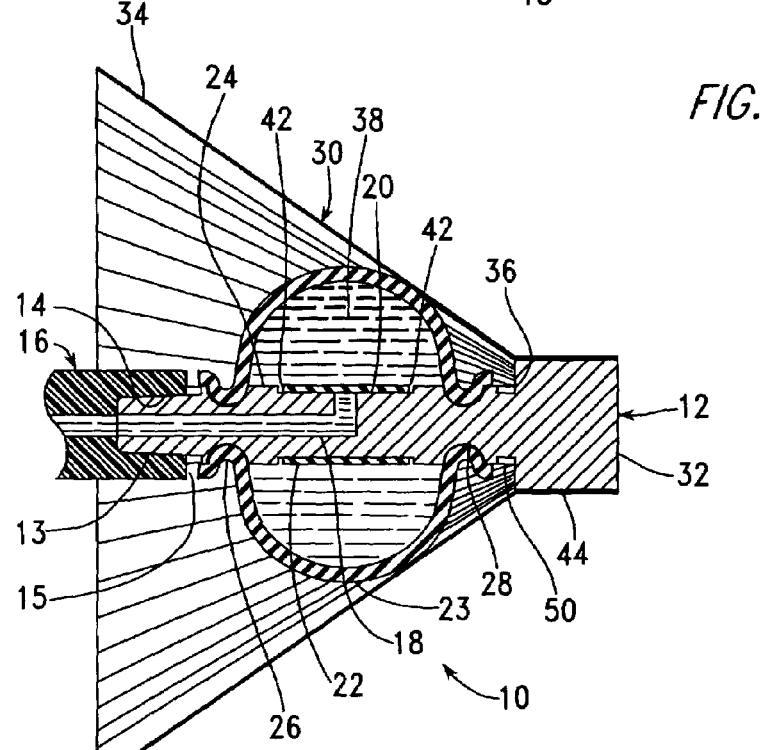
FIG. 2 is a longitudinal cross-sectional view of the bone plug of FIG. 1, with the inflatable sleeve in a fully inflated condition.

FIG. 2 is a longitudinal cross-sectional view of the bone plug 10 with the inflatable elastomeric sleeve 23 in a fully inflated condition. The inflation of the elastomeric sleeve 23 within the conical portion 34 of the shield 30 causes this portion 34 to expand as shown in FIG. 2. When the bone plug 10 is inserted within a bone channel during actual use, the bone channel limits the expansion of the conical portion 32 of the shield 30, causing its deflection into a partially cylindrical shape. At any level of inflation, the shield 30 extends around the inflatable elastomeric sleeve 23, protecting it from bone splinters or other sharp edges of a channel within the bone.

After the bone plug 10 is inserted into a bone channel, the inflatable elastomeric sleeve 23 is filled with a biocompatible fluid 38, such as saline solution, causing the sleeve 23 to extend from the uninflated condition of FIG. 1 to the inflated condition of FIG. 2. This inflation is accomplished by injecting the fluid 38 through the internal passage 18, so that pressure of the fluid 38 spreading between the cylindrical surface 20 of the core 12 and an internal surface 40 of the elastomeric valve sleeve 22 causes the expansion of the valve sleeve 22. This expansion allows the release of the fluid 38 past the ends 42 of the valve sleeve 22. When the pressure causing the injection of the fluid 38 through the internal passage 18 is stopped, the valve sleeve 22 closes, reducing the stresses previously causing its expansion, and preventing flow of the fluid 38 in either direction past the valve sleeve ends 42. In this way, the valve sleeve 22 acts as an internal check valve.

Thus, the inflatable elastomeric sleeve 23, together with the core 12, provide an inflatable structure which can be easily molded using conventional techniques, being removable from a central die or mandrel. The valve sleeve 22 is also easily molded. There is no need to form an enclosed structure with an internal valve, in the manner of the prior art device described in U.S. Pat. No. 4,697,584.

FIGS. 3 and 4 show the shield 30 in an undeflected condition (i.e. in the shape resulting from the manufacturing process, such as molding, with which it is made). FIG. 3 is a side elevation of the shield 30, while FIG. 4 is a proximal end elevation thereof.

Referring to FIGS. 1, 3, and 4, The shield 30 includes a distal cylindrical portion 44, which is attached to the distal end 32 of the core 12 (shown in FIG. 1) and a pleated conical portion 34, which extends outward in the undeflected condition at an included angle of, for example, 28 degrees. At the transition 46 between the cylindrical portion 44 and the conical portion 34, the pleats 48 extend inward, into a reduced-diameter cylindrical portion 50 of the core. The width of the individual pleats 48 increases linearly toward the proximal end 52 of the shield 30, providing more material to allow the conical portion 34 to be expanded. For example, each individual pleat 48 has a width of 0.76 mm (0.03 in.) at the transition 46, increasing to a width of 2.5 mm (0.10 in.) at the proximal end 52. The shield 30 is preferably molded from a flexible but tough material, such as polypropylene or a polyester resin, having a wall thickness of 0.25 mm (0.01 in.).

FIGS. 5 and 6 show the shield 30 in a fully compressed condition, with FIG. 5 being a side elevation and with FIG. 6 being a proximal end elevation. In the fully compressed condition, the pleated conical portion 34 extends outward at an included angle of, for example, 5 degrees. The shield 20 is compressed by the application of external forces, such as the forces produced as the bone plug 10 is slid into a gradually narrowing bone canal.

FIGS. 7 and 8 show the shield 30 in a fully extended condition, with FIG. 7 being a side elevation and with FIG. 8 being a proximal end elevation. In the fully extended condition, the pleated conical portion 34 outward at an included angle of, for example, 70 degrees. At the proximal end 52, the pleats 48 are essentially unfolded. The shield 20 is extended by the application of a force from within the pleated conical portion 34, as the inflatable elastomeric sleeve 23 is inflated.

Thus, the pleated conical shape of the proximal portion 34 allows a tough but flexible material to be used to form the shield 30. For the inflatable sleeve 23, an elastomeric material is used to allow the stretching necessary to accommodate the desired change in shape. Elastomeric materials are by nature relatively easily torn by sharp objects, such as bone splinters and other sharp edges which may protrude from the previously-prepared hole in a bone. The shield 30 thus provides substantial protection for the inflatable sleeve 23, being made of a material which is much more resistant to piercing or tearing by splinters and sharp edges.

FIG. 9 is a longitudinal cross-sectional elevation of the insertion device 16 used to insert the bone plug 10 of FIG. 1 into a previously-prepared channel within a bone. Referring to FIGS. 1 and 9, the distal end 15 of the insertion device 16 includes a tapered hole 14 for removably receiving the tapered end 13 of the bone plug 10. The proximal end 54 of the insertion device 16 includes a tapered hole 56, for removably receiving the tapered end of a conventional syringe, and a cylindrical knob 58 to facilitate handling the insertion device 16. The knob 58 may have a grooved or knurled outer surface. The insertion device 16, which is preferably molded from a thermoplastic resin, also includes a longitudinally extending hole 60, through which the fluid 38 is injected into the bone plug 10.

FIG. 10 is a fragmentary side elevation of the insertion device 16 of FIG. 9. Referring to FIGS. 9 and 10, the outer cylindrical surface 62 of the insertion device 16 includes a number of spaced-apart ribs 64, which are used to determine how far the insertion device 16 is inserted into a channel within bone. Preferably, the first rib 64, closest to the distal end 15, is 120 mm (4.73 in.) from the distal end 15, and sixteen additional ribs 64 extend from this rib 64 toward the proximal end 54 of the insertion device 16, being spaced along the length of the insertion device 16 at center-to-center distances of 10 mm (0.394 in.).

FIG. 11 is a fragmentary longitudinal cross-sectional elevation of an alternative version 66 of an insertion device. This alternative version 66 is similar to the insertion device 16, except that the distal end 68 is extended to include a pair of tabs 70 engaging an internally threaded section 72 of an alternative version 74 of the bone plug, and the proximal end 76 is similarly extended to include a pair of tabs 78 engaging a conventional internally threaded section 80 of a syringe 82. This alternative construction may be applied to either end of the insertion device, or to both ends, as shown in FIG. 11.

Figure 12:
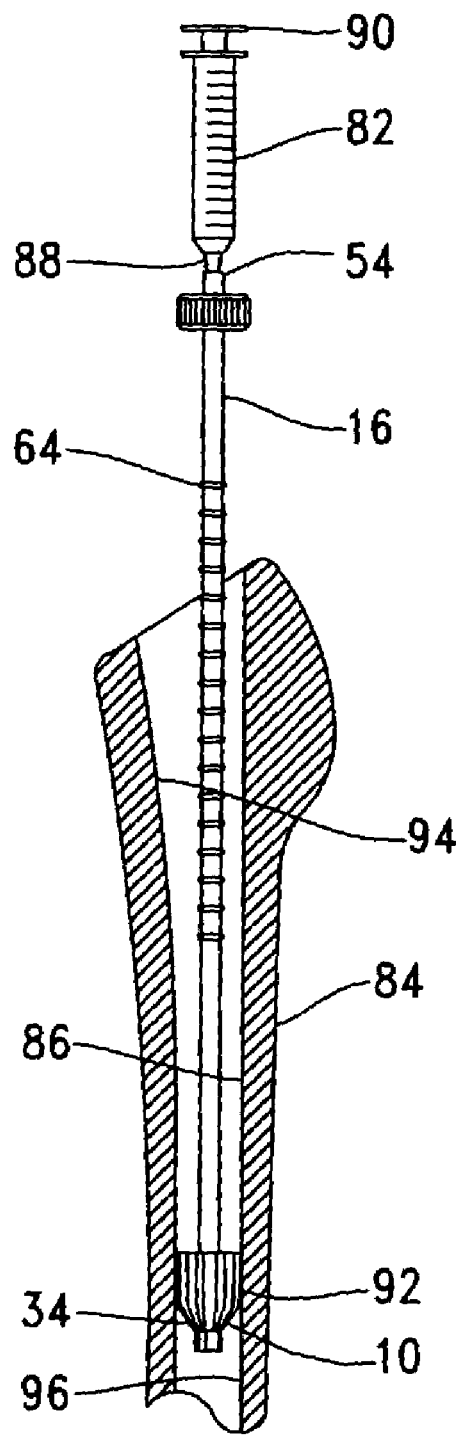
FIG. 12 is a longitudinal cross-sectional elevation of a femur including a previously-prepared channel, showing the insertion and inflation of the bone plug of FIG. 1 with the insertion device of FIG. 9.

FIG. 12 is a longitudinal cross-sectional elevation of a femur 84, including a previously-prepared channel 86, showing the insertion and inflation of the bone plug 10 of FIG. 1 with the insertion device 16 of FIG. 9. Referring to FIGS. 1 and 12, before this process is begun, the bone plug 10 is fastened to the distal end 15 (shown in FIG. 9) of the insertion device 16, with the bone plug 10 and the insertion device 16 being twisted relative to one another so that the tapered proximal end 13 of the bone plug 10 firmly engages the tapered hole 14 within the insertion device 16. Similarly, the syringe 82, filled with the fluid 38 used for inflating the inflatable elastomeric sleeve 23, is attached to the proximal end 54 of the insertion device 16, being twisted relative to the insertion device 16 so that a conventional tapered end 88 firmly engages the tapered hole 56 within the insertion tool 16.

Next, the insertion tool 16 is used to push the bone plug 10 into place, with the ribs 64 providing a visual indication of the depth to which the bone plug 10 is inserted. When the desired depth is reached, the plunger 90 of the syringe 82 depressed to inject the fluid 38 into the inflatable elastomeric sleeve 23 of the bone plug 10. Within the bone plug 10, the resulting inflation of the sleeve 23 pushes the pleated conical portion 34 of the shield 30 outward, to be held against the bone channel 86. A distal part 92 of the pleated conical portion 34 is forced into an essentially cylindrical configuration by contact with the channel 86, as flexure of the pleated conical portion occurs around the inflated elastomeric sleeve 23. After the bone plug 10 has been inflated in place, as shown in FIG. 12, the insertion tool 16 is twisted to unlock its connection with the bone plug 10, and the insertion tool 16 is removed. Then the prosthesis (not shown) is placed within the upper portion 94 of the bone channel 86, and the remaining space within this upper portion 94 is filled with bone cement. The presence of the bone plug 10 prevents the migration of this bone cement into the lower portion 96 of the bone channel 86.

The process of curing bone cement is exothermic, causing the local temperature to raise. In certain cases, this temperature increase may cause the formation of steam from the fluid 38 within the inflatable elastomeric sleeve 23. This sleeve 23 is preferably made to rupture in this event, so that extreme increases in pressure will not be transferred to surrounding bone. When the temperature has reached a such a high level, the surrounding bone cement has sufficiently hardened to make continued pressure within the inflatable sleeve 23 unnecessary to prevent leakage of cement around the plug 10.

Figure 13:
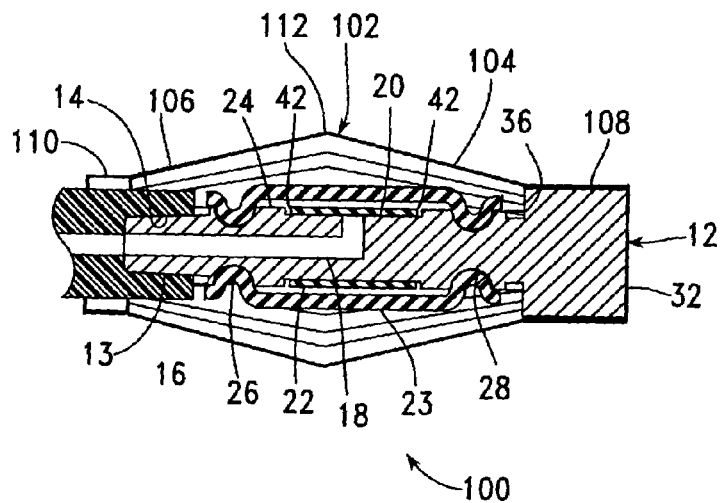
FIG. 13 is a longitudinal cross-sectional view of a bone plug made in accordance with a second embodiment of the present invention with an inflatable sleeve of the bone plug in a fully deflated condition.
Figure 14:
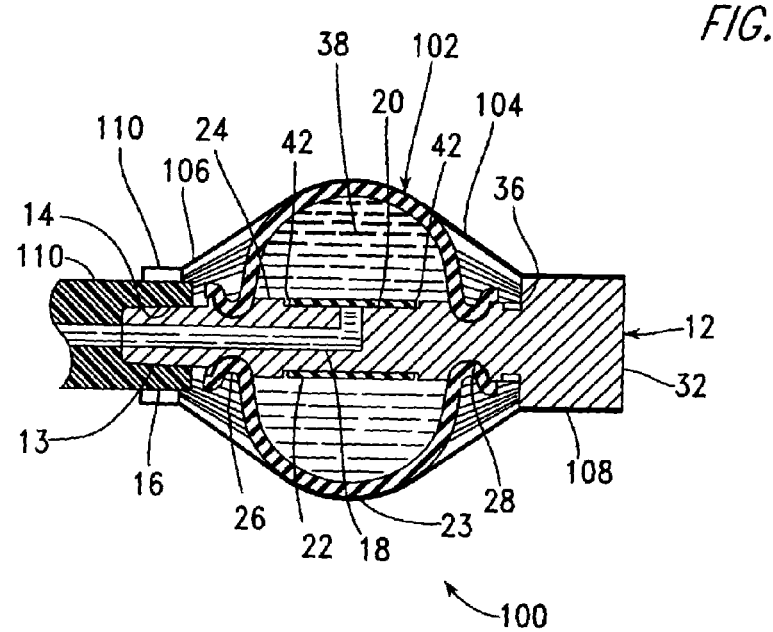
FIG. 14 is a longitudinal cross-sectional view of the bone plug of FIG. 13, with the inflatable sleeve in a fully inflated condition.

FIGS. 13 and 14 are longitudinal cross-sectional views of a second embodiment 100 of a bone plug built in accordance with the present invention. FIG. 13 shows the bone plug 100 with the inflatable elastomeric sleeve 23 in a deflated condition, while FIG. 14 shows the bone plug 100 with the sleeve in a fully deflated condition. This second embodiment 100 is similar to the first embodiment 10, with like parts being accorded like reference numerals, except that, in the second embodiment 100, the shield 30 having a single pleated conical section 34 is replaced by an alternative shield 102 having a distal pleated conical section 104 and a proximal pleated conical section 106. These pleated conical sections 104, 106 meet at their maximum openings, with the entire shield 102, including the conical sections 104, 106, preferably being made as a single part, together with a distal cylindrical section 108 and a proximal conical section 110. A forming process such as blow molding can be used to make the use of an internal die unnecessary.

During inflation of the elastomeric sleeve 23, flexure occurs in the region 112 of the shield 102, but there is no need to form the proximal half portion of the pleated section into a cylindrical shape, as discussed above in reference to FIG. 12. The distal cylindrical section 108 of the shield 100 is attached to the distal cylindrical portion 32 of the core 12. The proximal cylindrical section 110 of the shield 100 is allowed to slide along the insertion tool 16 with inflation of the elastomeric sleeve 23.

FIGS. 15–18 show a third embodiment 120 of a bone plug made in accordance with the present invention, in a fully deflated condition, with FIG. 15 being a side elevation thereof, with FIG. 16 being a distal end elevation thereof, with FIG. 17 being a transverse cross-sectional view thereof, taken as indicated by section lines XVII—XVII in FIG. 15, and with FIG. 18 being a longitudinal cross-sectional elevation thereof, taken as indicated by section lines XVIII—XVIII in FIG. 16.

The third embodiment bone plug 120 includes a central portion, generally indicated as 122, that is similar to a corresponding portion of the first embodiment bone plug 10, together with a shield, generally indicated as 124, comprising an outer shield structure 126 and an inner shield structure 128. Each of the shield structures 126, 128, which are coaxial with one another, includes a cylindrical end portion 130 at each end and a number of flexible beam portions 132 extending between the end portions 130. As particularly shown in FIG. 18, the outer shield structure 126 and the inner shield structure 128 each include six flexible beam portions 132 that are evenly spaced at sixty-degree angles around the structure 126, 128. The coaxial shield structures 126, 128 are further oriented so that the center 134 of each of the flexible beam portions 132 in the inner coaxial shield structure 128 lies directly inward from a gap 136 between adjacent flexible beam portions 132 in the outer coaxial shield structure 126. (While the coaxial shield structures 126, 128 are shown in cross-section in FIG. 18, cross-hatching that would otherwise obscure the relationships among the flexible beam portions 132 is not shown.) Preferably, the adjacent end portions 130 of the coaxial shield structures 126, 128 are fastened to one another to maintain this relationship. For example, these coaxial shield structures 126, 128 are composed of a molded thermoplastic resin, such as a high density polyethylene, being fastened together by ultrasonic welding or by an application of an adhesive between their end portions 130.

In the example of FIGS. 15–18, the shield 124 is slidably mounted on the central portion 122. Flanges 138 extend inward at each end of the shield 124 to restrain the sliding movement of the shield 124 on the central portion 122.

The central portion 122 includes a core 140 and a number of features that, being similar or identical to features of the first embodiment 10, described above in reference to FIG. 1, are accorded like reference numbers. For example, the core 140 includes an "L"-shaped internal passage 30 extending between its proximal end 142 and a recessed surface 20 underlying a valve sleeve 22. The core 140 also includes a groove 28 near each end, which is used to hold an inflatable elastomeric sleeve 23 in place to extend around the core 140 and over the valve sleeve 22.

In FIGS. 15 and 18, the bone plug 120 is shown attached to the distal end 144 of an insertion tool 146, which is similar to the insertion toll 16, described above in reference to FIGS. 9–11, except that an internally threaded hole 148 is provided therein for removably engaging a threaded proximal end portion 150 of the core 130.

FIGS. 19 and 20 are fragmentary longitudinal elevations of the central portion 122 of the bone plug 120, showing alternative versions of a retaining band holding the inflatable elastomeric sleeve 23 in place at each of the grooves 28 (shown in FIG. 18) within the core 140. In the example of FIG. 19, a retaining band 152 comprises several turns of wire tightly wound around the elastomeric sleeve 23 at the groove 28. In the example of FIG. 20, a retaining band 154 comprises a loop of wire with its ends 156 twisted to hold the elastomeric sleeve 23 at the groove 28.

FIGS. 21 and 22 show the bone plug 120 in a fully inflated condition, with FIG. 21 being a distal end view thereof, and with FIG. 22 being a longitudinal cross-sectional view thereof, taken as indicated by section lines XXII—XXII in FIG. 21.

The bone plug 120, in its deflated condition, is made ready for insertion by attachment to the distal end 144 of the insertion tool 146 by screwing the threaded proximal end portion 150 of the core 130 into place within the threaded hole 148 of the insertion tool 146. Next, in the general manner described above for the insertion of the bone plug 10 with the insertion tool 16, in reference to FIG. 12, the insertion tool 146 is used to insert the bone plug 120 into a prepared hole in bone to a desired level and to fill the inflatable elastomeric sleeve 23 with a biocompatable fluid 38. The valve sleeve 22 also functions as described above in reference to FIG. 2, allowing the fluid 38 to move past its ends 42 to fill the inflatable elastomeric sleeve 23 before preventing the return of the fluid 38 into the passageway 18.

As the inflatable elastomeric sleeve 23 is thus filled, the flexible beam portions 132 of the coaxial shield structure 126, 128 each bow radially outward. Central portions 158 of the flexible beam portions 132 of the outer coaxial shield structure 126 thus move apart from one another, as do the central portions 160 of the flexible beam portions 132 of the inner coaxial shield structure 128, so that the central portions 160 move outward into position between the adjacent central portions 158. In this way, both the central portions 158 and the central portions 160 bow into contact with the bone channel 86 (shown in FIG. 12).

After the bone plug 120 is filled in this way, the insertion tool 146 is unscrewed from the bone plug 120 and removed, with the bone plug 120 remaining in place through pressure against the bone channel 86, and with the fluid 38 being held within the bone plug 120 by the valve sleeve 22.

Figure 23:
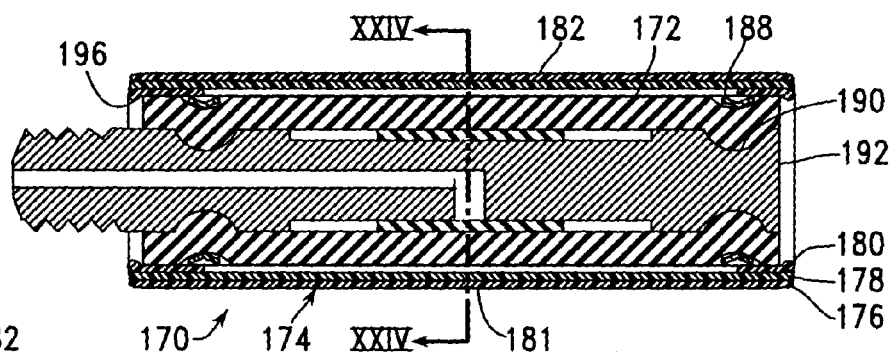
FIG. 23 is longitudinal cross-sectional view of a bone plug made in accordance with a fourth embodiment of the present invention, shown in a fully deflated condition.
Figure 24:
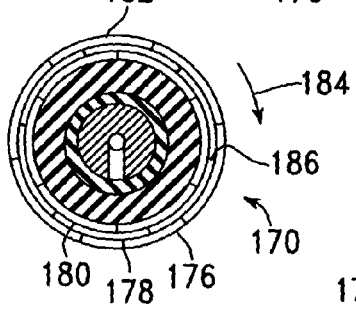
FIG. 24 is a transverse cross-sectional view of the bone plug of FIG. 23, shown in a fully deflated condition, taken as indicated by section lines XXIV—XXIV therein.

FIGS. 23 and 24 show a fourth embodiment 170 of a bone plug made in accordance with the invention un a fully deflated condition, with FIG. 23 being a longitudinal cross-sectional view thereof, and with FIG. 24 being a transverse cross-sectional view thereof, taken as indicated by section lines XXIV—XXIV in FIG. 23. This fourth embodiment bone plug 170 is similar to the third embodiment bone plug 120, described above in reference to FIGS. 15–22, except for modifications made to provide for the expansion of the bone plug 170 to fill a larger channel in a bone. Specifically, the inflatable elastomeric sleeve 172 is constructed to inflate to a larger diameter, and the shield 174 includes three coaxial shield structures, an outer coaxial shield structure 176, an intermediate coaxial shield structure 178, and in inner coaxial shield structure 178.

In the example of FIG. 24, the central portion 181 of each of the shield structures 176, 178, 180 is divided into six flexible beam portions 182, with each ov these beam portions extending around the bone plug 170, in the direction of arrow 184, through a sixty-degree angle. In each of the underlying shield structures 178, 180, each edge 186 of a flexible beam portion 182 is displaced from a corresponding edge 186 of an outwardly adjacent shield structure 176, 178 through a twenty-degree angle in the direction of arrow 184. (In FIG. 24, cross-hatching is omitted from the coaxial shield structures 176, 178, 180 to avoid obscuring the geometrical relationships among these structures.)

In general, this pattern is achieved in a bone plug having a first number of coaxial shield structures by dividing each of these coaxial shield structures into a number of flexible beam portions, each of which extends around the bone plug through a first angle, and by configuring the coaxial shield structures relative to one another so that, within each of the coaxial shield structures extending below the outermost of the coaxial shield structures, each of the beam portions has an edge displaced from a corresponding edge of a beam portion on an outwardly adjacent coaxial shield structure.

Figure 25:
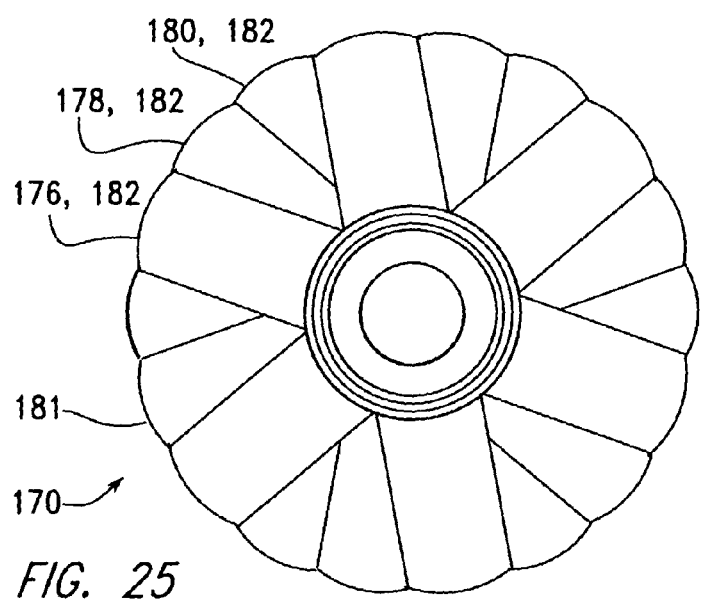
FIG. 25 is a distal end view of the bone plug of FIG. 25, shown in a fully inflated condition.

FIG. 25 is a distal end view of the fourth embodiment bone plug 170 in its fully inflated condition. Central portions 181 of each of the flexible beam portions are bowed radially outward, with central portions 181 of the flexible beam portions 182 within the outer coaxial shield structure 176 separating from one another to admit central portions 181 of flexible beam portions 182 within both the intermediate coaxial shield structure 178 and the inner coaxial shield structure 180 to move into place between these central portions 181 of the outer coaxial shield structure 176.

Figure 26:
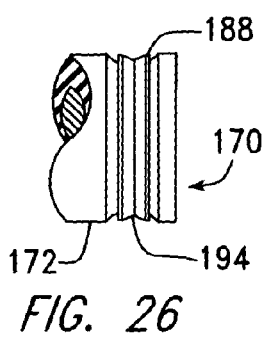
FIG. 26 is a fragmentary longitudinal elevation of a central portion of the bone plug of FIG. 15, showing a retaining band to hole an inflatable structure in place on a core therein.

FIG. 26 is a fragmentary longitudinal elevation of the bone plug 170 with the shield 174 removed to show a restraining band 188 used to hold the inflatable elastomeric sleeve 172 in place within each groove 188 in the underlying core 190 (shown in FIG. 23), and to prevent an escape of fluid from the inflated elastomeric sleeve 172. A depression 194 within the restraining band 188, which may be continuous around the band 188 or restricted to certain locations around the band 188, can be formed after the band 188 is moved into place.

In the example of FIG. 23, the shield 174 is slidably mounted on the inflatable elastomeric sleeve 172, with inward extending flanges 196 of the shield 174 restraining movement of the shield 174 along the sleeve 172. These flanges 196 may be formed as part of a process of joining the ends of the coaxial shield structures 176, 178, 180 so that the angular relationships among these structures, described above in reference to FIGS. 24 and 25 are maintained.

Figure 27:
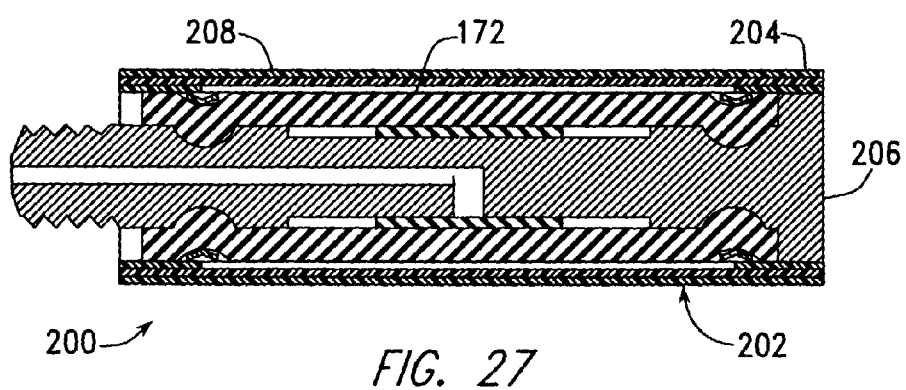
FIG. 27 is a longitudinal cross-sectional view of a bone plug having a shield attached to a core therein at one end thereof.

FIG. 27 is a longitudinal cross-sectional view of a bone plug 200 having a shield 202 attached at a first end 204 to an underlying core 206. The remaining portion 208 of the shield 202 is slidable on the underlying inflatable elastomeric sleeve 172. Other aspects of this alternative bone plug 200 are similar to those of the bone plug 170, described above in reference to FIGS. 23–25.

While the present invention has been described in its preferred forms or embodiments with some degree of particularity, it is understood that this description has been given only by way of example and that numerous changes in the details of construction, fabrication, and use, including changes in the combination and arrangement of parts, may be made without departing from the spirit and scope of the invention as described in the appended claims. For example, it is understood that the retaining band structures described above in reference to FIGS. 19, 20, and 26, and the use of screw treads for removable attachment to an insertion tool, may be applied to the first and second embodiments of the invention, as described in reference to FIGS. 1 and 13.

I claim:

1. Apparatus for plugging a channel within a bone to stop a flow of bone cement through said channel, wherein said apparatus comprises:
    an inflatable structure;
    an insertion tool including a channel for filling said inflatable structure with a fluid;
    a core removably attaching said insertion tool to said inflatable structure;
    a shield including a plurality of coaxial shield structures, each extending outwardly around and along said inflatable structure, wherein each of said coaxial shield structures includes a distal end portion, a proximal end portion and a number of flexible beam portions extending longitudinally along said inflatable structure between said distal end portion and said proximal end portion, wherein said flexible beam portions of said coaxial shield structures curve outwardly with inflation of said inflatable structure, with central portions of said flexible beam portions within each of said coaxial shield structures separating from one another, and with said central portions of said flexible beam portions of one of said coaxial shield structures extending outward between adjacent central portions of said flexible beam portions of another of said coaxial shield structures, wherein said shield is substantially more resistant to damage from sharp objects than said inflatable structure, wherein said elongated insertion tool is removably connected to said core, and wherein said elongated insertion tool includes a tool passageway for said fluid injected into said core passageway.

2. The apparatus of claim 1, wherein said core includes a valve admitting a fluid into said inflatable structure and preventing a flow of fluid from said inflatable structure.

3. The apparatus of claim 1, wherein
    said shield comprises an outer coaxial shield structure and an inner coaxial shield structure, and
    a center of each of said flexible beam portions within said inner coaxial shield structure extends beneath a gap between adjacent flexible beam portions within said outer coaxial shield structure.

4. The apparatus of claim 1, wherein
    said shield comprises a first number of coaxial shield structures,
    each of said flexible beam structures extends around said inflatable structure through a first angle, and
    each of said flexible beam structures in a coaxial shield structure extending below an outermost coaxial shield structure includes an edge displaced in a first direction, through said first angle divided by said first number, around said inflatable structure, from an edge of another flexible beam structure outwardly adjacent said flexible beam structure.

5. Apparatus for plugging a channel within a bone to stop a flow of bone cement through said channel, wherein
    said apparatus comprises a bone plug, insertable within said channel, and an elongated insertion tool,
    said bone plug includes an inflatable structure, a core attached to said inflatable structure, a shield including a plurality of coaxial shield structures, each extending outwardly around and along said inflatable structure, and a valve admitting a fluid into said inflatable structure and preventing a flow of fluid from said inflatable structure,
    said core includes a core passageway for said fluid injected into said inflatable structure,
    each of said coaxial shield structures includes a distal end portion, a proximal end portion and a number of flexible beam portions extending longitudinally along said inflatable structure between said distal end portion and said proximal end portion,
    said flexible beam portions of said coaxial shield structures curve outwardly with inflation of said inflatable structure, with central portions of said flexible beam portions within each of said coaxial shield structures separating from one another, and with said central portions of said flexible beam portions of one of said coaxial shield structures extending outward between adjacent central portions of said flexible beam portions of another of said coaxial shield structures,
    said shield is substantially more resistant to damage from sharp objects than said inflatable structure,
    said elongated insertion tool is removably connected to said core, and
    said elongated insertion tool includes a tool passageway for said fluid injected into said core passageway.

6. The apparatus of claim 5, wherein said inflatable structure extends as a sleeve over said core, being fastened to said core at proximal and distal ends of said inflatable structure.

7. The apparatus of claim 6, wherein
    said core additionally includes a first groove extending around a circumference of a proximal end of said core and a second groove extending around a circumference of a second end of said core, and
    said bone plug additionally includes a first retaining band extending around a proximal end of said inflatable structure to hold said inflatable structure within said first groove and a second retaining band extending around a distal end of said inflatable structure.

8. The apparatus of claim 6, wherein
    said valve extends as a sleeve over said core passageway within said inflatable structure, blocking movement of said fluid from said inflatable structure into said core passageway, and
    said fluid flows through said sleeve and out an end of said sleeve into said inflatable structure from said core passageway.

9. The apparatus of claim 8, wherein said valve is composed of an elastomer.

10. The apparatus of claim 5, wherein
    said core and said inflatable structure comprise a central structure of said bone plug,
    said distal end portion of each of said coaxial shield structures extends around and along a distal portion of said central structure, and said proximal end portion of each of said coaxial shield structures extends around and along a proximal portion of said central structure.

11. The apparatus of claim 10, wherein said shield includes
   a distal end portion, slidably mounted on said distal end portion of said central structure, having a distal flange extending inward to restrain movement along said distal end portion of said central structure, and
   a proximal end portion slidably mounted on said proximal end portion of said central structure, having a proximal flange extending inward to restrain movement along said proximal end portion of said central structure.

12. The apparatus of claim 10, wherein said shield includes
   a first end portion attached to a first end portion of said central structure, and
   a second end portion slidably mounted on an end portion of said central structure opposite said first end portion of said central structure.

13. The apparatus of claim 5, wherein
   said shield comprises an outer coaxial shield structure and an inner coaxial shield structure, and
   a center of each of said flexible beam portions within said inner coaxial shield structure extends beneath a gap between adjacent flexible beam portions within said outer coaxial shield structure.

14. The apparatus of claim 5, wherein
   said shield comprises a first number of coaxial shield structures,
   each of said flexible beam structures extends around said inflatable structure through a first angle, and
   each of said flexible beam structures in a coaxial shield structure extending below an outermost coaxial shield structure includes an edge displaced in a first direction, through said first angle divided by said first number, around said inflatable structure, from an edge of another flexible beam structure outwardly adjacent said flexible beam structure.

15. The apparatus of claim 5, wherein
   each of said coaxial shield structures is composed of a molded thermoplastic resin, and
   end portions of said coaxial shield structures are attached to one another.

16. The apparatus of claim 15, wherein said molded thermoplastic resin is a high density polyethylene.

17. The apparatus of claim 5, wherein said core and said elongated insertion tool each include threaded surfaces removably connecting said elongated insertion tool to said core.

18. Apparatus for plugging a channel within a bone to stop a flow of bone cement through said channel, wherein
   said apparatus comprises a bone plug, insertable within said channel, and an elongated insertion tool,
   said bone plug includes an inflatable structure, a core attached to said inflatable structure, a shield extending from a distal portion of said core outwardly around and along said inflatable structure, and a valve admitting a fluid into said inflatable structure and preventing a flow of fluid from said inflatable structure,
   said core includes a core passageway for said fluid injected into said inflatable structure, a first groove extending around a circumference of a proximal end of said core, and a second groove extending around a circumference of a second end of said core,
   said bone plug additionally includes a first retaining band extending around a proximal end of said inflatable structure to hold said inflatable structure within said first groove and a second retaining band extending around a distal end of said inflatable structure,
   said shield is substantially more resistant to damage from sharp objects than said inflatable structure,
   said elongated insertion tool is removably connected to said core, and
   said elongated insertion tool includes a tool passageway for said fluid injected into said core passageway.

19. The apparatus of claim 18, wherein
   said valve extends as a sleeve over said core passageway within said inflatable structure, blocking movement of said fluid from said inflatable structure into said core passageway, and
   said fluid flows through said sleeve and out an end of said sleeve into said inflatable structure from said core passageway.

20. The apparatus of claim 18, wherein said core and said elongated insertion tool each include threaded surfaces removably connecting said elongated insertion tool to said core.

\* \* \* \* \*